United States Patent [19]

Yamada et al.

[11] Patent Number: 5,194,653

[45] Date of Patent: Mar. 16, 1993

[54] CARBONATES OF ACETYLENIC ALCOHOLS

[75] Inventors: Mitsuo Yamada, Osaka; Kei Aoki, Nara; Satoshi Urano; Ryuzo Mizuguchi, both of Kyoto, all of Japan

[73] Assignee: Nippon Paint Company, Limited, Osaka, Japan

[21] Appl. No.: 923,435

[22] Filed: Aug. 3, 1992

Related U.S. Application Data

[62] Division of Ser. No. 699,395, May 14, 1991.

Foreign Application Priority Data

May 17, 1990 [JP]  Japan .................. 2-127781
May 17, 1990 [JP]  Japan .................. 2-127785

[51] Int. Cl.$^5$ ............................................ C07C 69/96
[52] U.S. Cl. ..................................................... 558/268
[58] Field of Search ......................................... 558/268

[56] References Cited

PUBLICATIONS

CA 94(12):85076t (Berlin et al).
CA 100(6):34952k (Sherle et al).

*Primary Examiner*—José G. Dees
*Assistant Examiner*—Joseph Conrad, III
*Attorney, Agent, or Firm*—Millen, White, Zelano and Branigan

[57] ABSTRACT

Polymerizable carbonate compounds of the formula:

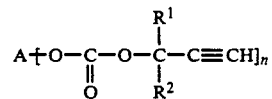

wherein A is an aromatic polycycle, $R^1$ and $R^2$ are independently hydrogen atom or alkyl, and n is 1, 2 or 3, are disclosed. They are useful as a component of nonemanating, self-curing and heat resistant resin compositions.

8 Claims, No Drawings

CARBONATES OF ACETYLENIC ALCOHOLS

This is a division of application Ser. No. 07/699,395, filed May 14, 1991.

BACKGROUND OF THE INVENTION

This invention relates to novel carbonates of acetylenic alcohols.

It has been known that certain compounds having acetylenically unsaturated groups such as ethynyl or propynyl group may be polymerized into a conjugated diene polymer. Because of their unique polymerization mechanism and the unique electrical and physical properties of their polymers, such compounds are attracting a great interest as a component for producing self-curable, nonemanating resinous compositions. Japanese Patent Kokai No. 108213/89, for example, discloses a propargyl ether of cresol novolac resin as one of such compounds.

The present invention provides a novel class of compounds in which an acetylenic alcohol moity is attached to a phenolic moiety via a carbonate linkage to improve the heat resistance of the resultant polymers.

SUMMARY OF THE INVENTION

According to the present invention, there is provided a compound of the formula:

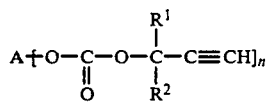

wherein

A is an aromatic polycyclic system selected from the group consisting of a fused carbocycle having more than one benzene rings arranged in a straight row, a system having two benzene rings linked together with a direct bond, a $C_1$-$C_{20}$ alkylidene group, a cyclohexylidene group,

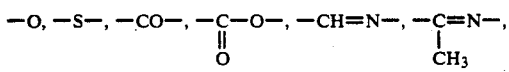

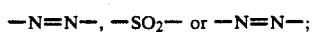

and derivatives thereof having on their benzene ring up to four substituents selected from the group consisting of a $C_1$-$C_{12}$ alkyl, a $C_1$-$C_{12}$ alkoxy, halo, nitro and cyano;

$R^1$ and $R^2$ are independently a hydrogen atom or $C_1$-$C_{12}$ alkyl; and n is an integer of 1, 2 or 3.

The compound of this invention may be synthesized by reacting a phenol of the formula:

wherein A and n are as defined, with a chloroformate of the formula:

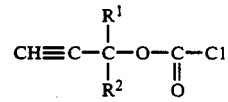

wherein $R^1$ and $R^2$ are as defined, in the presence of an acid acceptor, or alternatively reacting a chloroformate of the formula:

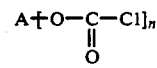

wherein A and n are as defined, with an alcohol of the formula:

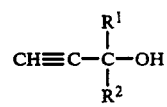

wherein $R^1$ and $R^2$ are as defined, in the presence of an acid acceptor.

DETAILED DISCUSSION

The compounds of the invention are carbonate esters of an acetylenic alcohol such as propargyl alcohol and a mono- di or triphenol. Such carbonate esters may be synthesized, as is well-known, by reacting phosgene with either one of the phenol or the acetylenic alcohol to produce the corresponding chloroformate followed by the reaction of the latter with the other in the presence of an acid accepter.

As one class of the starting phenols, the present invention employs a polycyclic phenol capable of providing molecular orientating, liquid crystalline and optically anisotropic properties to the carbonate polymers. It has been known that such properties may be given by incorporating into the polymer chain a plurality of biphenyl groups or a fused carbocycle system having more than one benzene ring in a linear arrangement such as naphthalene, anthracene, naphthacene and the like. Phenols of this class are those derived from biphenyl or the fused carbocycle system, or the corresponding phenols having up to four substituents selected from the group consisting of a $C_1$-$C_{12}$ alkyl, a $C_1$-$C_{12}$ alkyoxy, halo, nitro and cyano.

Specific examples of phenols of this class include:
O-phenylphenol,
m-phenylphenol,
p-phenylphenol,
4,4-hydroxybiphenyl,
2,2'-hydroxybiphenyl,
3-chloro-4,4'-dihydroxybiphenyl,
α-naphthol,
β-naphtol,
2,6-dihydroxynaphthalene,
2,7-dihydroxynaphthalene,
2-hydroxyanthracene,
9-hydroxyanthracene,
1,2-dihydroxyanthracene,
1,4-dihydroxyanthracene,
1,5-dihydroxyanthracene,
1,8-dihydroxyanthracene,
2,3-dihydroxyanthracene,
2,6-dihydroxyanthracene, 2,7-dihydroxyanthracene,
1,9-dihydroxyanthracene,
9,10-dihydroxyanthracene, and the like.

Another class of starting phenols used in the present invention include bisphenols in which two benzene rings are linked through a bridge selected from the group consisting of a $C_1$–$C_{20}$ alkylidene group, a cyclohexylidene group,

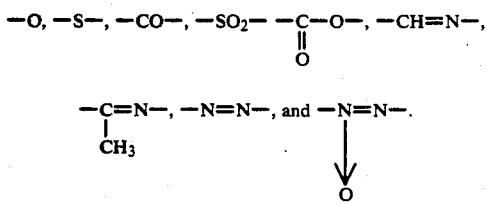

Again the bisphenols may have on the benzene ring up to four substituents selected from the group consisting of a $C_1$–$C_{12}$ alkyl, a $C_1$–$C_{12}$ alkoxy, halo, nitro and cyano.

Specific examples of bisphenols include:
bis(4-hydroxylphenyl)methane;
bis(4-hydroxy-2-methylphenyl)methane;
1,1-bis(4-hydroxyphenyl)ethane;
1,1-bis(4-hydroxy-3-methyl-5-t-butylphenyl)butane;
bis(4-hydroxy-2-chlorophenyl)methane;
bis(4-hydroxyphenyl)tridecane;
bis(2-hydroxyphenyl)methane;
bis(3-hydroxyphenyl)methane;
bis(2-hydroxy-4-methylphenyl)methane;
bis(2-hydroxy-5-methylphenyl)methane;
bis(2-hydroxy-6-methylphenyl)methane;
bis(4-hydroxy-3-methylphenyl)methane;
bis(3-hydroxy-2,4,6-trimethylphenyl)methane;
bis(2-hydroxy-4-propylphenyl)methane;
bis(4-hydroxy-2-propylphenyl)methane;
bis(4-hydroxy-2-methyl-6-ethylphenyl)methane;
bis(4-hydroxy-2,3,5,6-tetramethylphenyl)methane;
bis(2-hydroxy-4-t-butylphenyl)methane;
bis(4-hydroxy-2-methyl-5-isopropylphenyl)methane;
bis(4-hydroxy-2-t-butyl-5-methylphenyl)methane;
bis(4-hydroxy-2,6-di-t-butylphenyl)methane;
bis(4-hydroxy-2,6-dichropheyl)methane;
bis(2-hydroxy-4-bromophenyl)methane;
bis(3-hydroxy-2,4,6-trichlorophenyl)methane;
bis(4-hydroxy-2-methoxyphenyl)methane;
1,1-bis(4-hydroxyphenyl)cyclohexane;
2,2'-thiobisphenol;
4,4'-thiobisphenol;
4,4'-thiobis(2-methylphenol);
2,2'-thiobis(4,5-dimethylphenol);
2,2'-thiobis(4,6-dimethylphenol);
4,4'-thibis(2,6-dimethylphenol);
2,2'-thiobis(6-t-butyl-4-methylphenol);
4,4'-thiobis(2-t-butyl-5-methylphenol);
2,2'-thiobis(4-fluorophenol);
2,2'-thiobis(4-chlorophenol);
4,4'-thiobis(3-chlorophenol);
2,2'-thiobis(4,6-dichlorophenol);
4,4'-thiobis(2-bromophenol);
2,2'-thiobis(5-nitrophenol);
bis(4-hydroxyphenyl)sulfone;
bis(2-hydroxyphenyl)sulfone;
bis(4-hydroxy-2-methylphenyl)sulfone;
bis(4-hydroxy-2,5-dimethylphenyl)sulfone;
bis(4-hydroxy-2-t-butyl-5-methylphenyl)sulfone;
bis(4-hydroxy-2-chlorophenyl)sulfone;
bis(4-hydroxy-3-chlorophenyl)sulfone;
bis(4-hydroxy-2-bromophenyl)sulfone;
bis(4-hydroxy-2-nitrophenyl)sulfone;
4,4'-dihydroxybenzophenone;
2,2'-dihydroxy-4-methoxybenzophenone;
4,4'-dihydroxydiphenyl ether;
4,4'-dihydroxyphenylbenzoate;
4,4'-dihydroxyazobenzene;
4,4'-dihydroxyazoxybenzene;
4'-hydroxybenzylidene-4'-hydroxyaniline;
4'-hydroxy-α-methylbenzylidene-4-hydroxyaniline;
4,4-dihydroxydiphenyl sulfide; and the like.

Acetylenic alcohols used in the synthesis of the carbonates of this invention include propargyl alcohol and its α-mono- and α,α-di-$C_1$–$C_{20}$ alkyl derivatives. Propargyl alcohol is preferred.

The carbonate compounds of this invention are synthesized by reacting either one of the phenol component and the acetylenic alcohol component with phosgene to form the corresponding chloroformate following by reacting the latter with the other component. The reaction of the chloroformate of acetylenic alcohol with the phenol is preferred.

The reaction may be performed, as is conventional, in an inert solvent in the presence of an acid acceptor.

Examples of usable inert solvents include DMSO, DMF, N-methylpyrrolidone, acetone, methyl ethyl ketone, methyl isobutyl ketone, benzene, toluene, xylene, diethyl ether, tetrahydrofuran, dioxane, methylene chloride, dichloroethane and the like. When the reaction system is not too viscous, the reaction may be performed without using the solvent.

Examples of acid acceptors include trimethylamine, triethylamine, pyridine, sodium hydroxide, potassium hydroxide, calcium hydroxide, magnesium hydroxide, sodium silicate, sodium aluminate, sodium carbonate, potassium carbonate, alkali metal ethoxide and the like. Tertiary amines and pyridine are preferred.

The reaction is preferably carried out under the nitrogen gas atmosphere to prevent coloration of the product. The reaction temperature may range from room temperature to the boiling point of the solvent used.

After the reaction, the product may be isolated and purified by the conventional technique such as extraction, recrystallization and the like.

The carbonate compounds thus prepared may be polymerized with a metallic catalyst or initiator, or by irradiating with actinic radiations such as UV radiation, gamma radiation or electron beam radiation. They are, therefore, useful as stock materials of resins used in paints, electric and electronic components, structural materials and nonlinear optical materials where nonemanating cure, and durability and heat restance properties are desired in the finished products.

The invention is illustrated by the following examples wherein all parts and percents are by weight unless otherwise specified.

EXAMPLE 1

Bis(4-propargyloxycarbonyloxyphenyl)methane

A flask equipped with a stirrer, thermoter, nitrogen gas tube and reflux condenser was charged with 20.0 g of bis(4-hydroxyphenyl)methane, 50.0 g of methylene chloride and 23.0 g of trimethylamine. To the flask was added 26.0 g of propargyl chloroformate dropwise over one hour and the mixture was allowed to react for 6 hours at 30° C. After the reaction, the reaction mixture was treated with methylene chloride-water mixture and the organic phase was separated followed by drying over magnesium sulfate overnight. After filtering, the filtrate was evaporated in a rotary evaporator. The resulting crystals were recrystallized to give the title compound melting at 60° C. at a yield of 93.6% of theory.

The structure of the product was identified by the IR spectrum and $^1$H-NMR (in CDCl$_3$, trimethylsilane standard).

IR: 2980 cm$^{-1}$ (—CH$_2$—); 3300 cm$^{-1}$, 2100 cm$^{-1}$ (CH≡C—); 1738 cm$^{-1}$ (—OCOO—); 1600 cm$^{-1}$, 1500 cm$^{-1}$ (Phe); 1450 cm$^{-1}$ (—CH$_2$—).

$^1$H-NMR: δ(ppm) 2.41 (CH≡C—); 4.87 (—CH$_2$—); 6.96, 7.15 (Phe); 2.54 (—CH$_2$—).

EXAMPLE 2

Bis(4-proparagyloxycarbonyloxy-2-methylphenyl)methane

The title compound was produced by reacting 23.0 g of bis(4-hydroxy-2-methylphenyl)methane and 26.0 g of propargyl chloroformate in 50.0 g of methylene chloride in the presence of 23.0 g of trimethylamine as in Example 1. Yield was 83.6% of theory.

IR: 2990 cm$^{-1}$ (—CH$_3$); 3320 cm$^{-1}$, 2100 cm$^{-1}$ (CH≡C—); 1740 cm$^{-1}$ (—OCOO—); 1600 cm$^{-1}$, 1500 cm$^{-1}$ (Phe); 1450 cm$^{-1}$ (—CH$_3$).

$^1$H-NMR: δ(ppm) 2.42 (CH≡C—); 4.89 (—CH$_2$—); 6.75, 7.13 (Phe); 2.64 (—CH$_2$—); 1.64 (—CH$_3$).

EXAMPLE 3

Bis(4-propargyloxycarbonyloxyphenyl)sulfone

The title compound was produced by reacting 20.0 g of bis(4-hydroxyphenyl)sulfone and 26.6 g of propargyl chloroformate in 50.0 g of methylene chloride in the presence of 23.0 g of trimethylamine as in Example 1. m.p. 112°–114° C. Yield was 73.6% of theory.

IR (cm$^{-1}$): 3300, 2110 (CH≡C—); 1738 (—OCOO—); 1600, 1500 (Phe); 1350 (—SO$_2$—).

$^1$H-NMR: δ(ppm) 2.55 (CH≡C—); 4.86 (—CH$_2$—); 7.30, 7.90 (Phe).

EXAMPLE 4

4,4'-Bis(propargyloxycarbonyloxy)benzophenone

The title compound was produced by reacting 23.0 g of 4,4'-dihydroxybenzophenone and 26.0 g of propargyl chloroformate in 50.0 g of methylene chloride in the presence of 23.0 g of trimethylamine as in Example 1. m.p. 104°–106° C. Yield was 83.6% of theory.

IR (cm$^{-1}$): 3300, 2100 (CH≡C—); 1755 (—OCOO—); 1610, 1510 (Phe).

$^1$H-NMR, δ(ppm): 2.42 (CH≡C—); 4.89 (—CH$_2$—); 7.30, 7.90 (Phe).

Analogous to Example 1, following compound were produced

EXAMPLE 5

1,1-Bis(4-propargyloxycarbonyloxyphenyl)cyclohexane

IR (cm$^{-1}$): 3300, 2100 (CH≡C—); 1740 (—OCOO—); 1610, 1500 (Phe); 2920, 1450 (—CH$_2$—).

$^1$H-NMR, δ(ppm): 2.42 (CH≡C—); 4.89 (—CH$_2$—); 6.90, 7.12 (Phe).

EXAMPLE 6

1,1-Bis(4-propargyloxycarbonyloxyphenyl)ethane

IR (cm$^{-1}$): 3300, 2100 (CH≡C—); 1750 (—OCOO—); 1610, 1500 (Phe); 2980 (—CH$_3$).

$^1$H-NMR, δ(ppm): 1.11 (—CH$_3$); 2.40 (CH≡C—); 4.90 (—CH$_2$—); 6.90, 7.22 (Phe).

EXAMPLE 7

1,1-Bis(4-propargyloxycarbonyloxy-3-butylphenyl)butane

IR (cm$^{-1}$): 3300, 2100 (CH≡C—); 1750 (—OCOO—); 1610, 1500 (Phe); 2980 (—CH$_3$); 1240 (t-butyl).

$^1$H-NMR, δ(ppm): 1.11 (—CH$_3$); 2.40 (CH≡CO—); 4.90 (—CH$_2$—); 6.85, 7.12 (Phe).

EXAMPLE 8

Bis(2-chloro-4-propargyloxycarbonyloxyphenyl)methane

IR (cm$^{-1}$): 3300, 2100 (CH≡C—); 1750 (—OCOO—); 1600, 1500 (Phe), 1100 (Cl).

$^1$H-NMR, δ(ppm): 2.42 (CH≡C—); 2.60 (—CH$_2$—); 4.88 (≡C—CH$_2$—); 6.78, 7.10 (Phe).

EXAMPLE 9

1,1-Bis(4-propargyloxycarbonyloxyphenyl)tridecane

IR (cm$^{-1}$): 3300, 2110 (CH≡C—); 1750 (—OCOO—); 1610, 1500 (Phe).

$^1$H-NMR, δ(ppm): 2.40 (CH≡C—); 4.90 (≡C—CH$_2$—); 6.90, 7.22 (Phe).

EXAMPLE 10

4,4'-Bis(propargyloxycarbonyloxy)diphenyl ether

IR (cm$^{-1}$): 3300, 2110 (CH≡C—); 1765 (—OCOO—); 1610, 1510 (Phe); 1250 (—O—).

$^1$H-NMR, δ(ppm): 2.42 (CH≡C—); 4.89 (≡C—CH$_2$—); 7.10, 7.85 (Phe).

EXAMPLE 11

4,4'-Bis(propargyloxycarbonyloxy)diphenylsulfide

IR (cm$^{-1}$): 3300, 2110 (CH≡C—); 1760 (—OCOO—); 1610, 1510 (Phe).

$^1$H-NMR, δ(ppm): 2.40 (CH≡C—); 4.87 (≡C—CH$_2$—); 7.10, 7.95 (Phe).

EXAMPLE 12

4,4'-Bis(propargyloxycarbonyloxy)phenyl benzoate

IR (cm$^{-1}$): 3300, 2100 (CH≡C—); 1760–1720 (—OCOO—); 1600, 1500 (Phe).

$^1$H-NMR, δ(ppm): 2.39 (CH≡C—); 4.72 (≡C—CH$_2$—); 7.20, 7.88 (Phe).

EXAMPLE 13

4,4'-Bis(propargyloxycarbonyloxy)azobenzene

IR (cm$^{-1}$): 3300, 2100 (CH≡C—); 1760 (—OCOO—); 1600, 1510 (Phe).

$^1$H-NMR, δ(ppm): 2.39 (CH≡C—); 4.72 (≡C—CH$_2$—); 7.20, 7.90 (Phe).

EXAMPLE 14

4,4'-Bis(propargyloxycarbonyloxy)azoxybenzene

IR (cm$^{-1}$): 3300, 2100 (CH≡C—); 1760 (—OCOO—); 1610, 1510 (Phe).

1H-NMR, δ(ppm): 2.42 (CH≡C—); 4.88 (≡C—CH₂—); 7.10, 7.95 (Phe).

EXAMPLE 15

N-(4-propargyloxycarbonyloxybenzylidene)-4-propargyloxycarbonyloxyaniline

IR (cm⁻¹): 3300, 2100 (CH≡C—); 1760 (—O-COO—); 1610, 1510 (Phe).
¹H-NMR, δ (ppm): 2.42 (CH≡C—); 4.85 (≡C—CH₂—); 7.10, 7.85 (Phe).

EXAMPLE 16

Bis(3,3-dibromo-4-propargyloxycarbonyloxyphenyl)-sulfone

IR (cm⁻¹): 3300, 2200 (CH≡C—); 1760 (—O-COO—); 1610, 1510 (Phe).
¹H-NMR, δ(ppm): 2.40 (CH≡C—); 4.78 (≡C—CH₂—); 7.20, 7.85 (Phe).

EXAMPLE 17

Bis[4-(1,1-dimethyl-2-propinyl)oxycarbonyloxyphenyl]sulfone

IR (cm⁻¹): 3300, 2100 (CH≡C—); 1738 (—O-COO—); 1600, 1500 (Phe); 1350, 1150 (—SO₂—).
¹H-NMR, δ(ppm): 1.30 (—CH₃); 2.55 (CH≡C—); 4.86 (≡C—CH₂—); 7.30, 7.90 (Phe).

EXAMPLE 18

Analogous to Example 1, diphenylsulfone-4,4'-bis-chloroformate was reacted with propargyl alcohol. The product was identified to be the same as the product of Example 3.

EXAMPLE 19

4,4'-Bis(propargyloxycarbonyloxy)biphenyl

A flask equipped with a stirrer, thermometer, nitrogen gas tube and reflux condenser was charged with 18.6 g of 4,4'-dihydroxybiphenyl and 23.0 g of trimethylamine in 50.0 g of methylene chloride. To the flask was added 26.0 g of propargyl chloroformate dropwise over one hour and the mixture was allowed to react for 6 hours at 30° C. After the reaction, the reaction mixture was treated with methylene chloride-water mixture and the organic phase was separated followed by drying over magnesium sulfate overnight. After filtering, the filtrate was evaporated in a rotary evaporator. The resulting crystals were recrystallized to give the title compound at a yield of 93.6% of theory.

IR (cm⁻¹) 3330, 2110, 1750, 1600, 1500.
¹H-NMR (δ, ppm) 2.55 (CH≡C—), 4.86 (≡C—CH₂—), 7.30, 7.90 (Ph).

EXAMPLE 20

2,7-Bis(propargyloxycarbonyloxy)naphthalene

Analogous to Example 19, 2,7-dihydroxynaphthalene was reacted with propargyl chloroformate to produce the title compound. Yield was 83.6% theory. m.p. 94°-96° C.

IR (cm⁻¹) 3330, 2100, 1755, 1610, 1510.
¹H-NMR (δ, ppm) 2.42 (CH≡C—), 4.86 (≡C—CH₂—), 7.20, 8.10 (Ph).

Analogous to Example 19, the following compounds were synthesized.

EXAMPLE 21

1,8-Bis(propargyloxycarbonyoxy)anthracene

Yield, 88.3%.
NMR (cm⁻¹) 3300, 2100, 1760, 1610, 1510.
¹H-NMR (δ, ppm) 2.42 (CH≡C—), 4.89 (≡C—CH₂—), 7.10, 8.20 (Ph).

EXAMPLE 22

3-Chloro-4,4'-bis(propargyloxycarbonyloxy)biphenyl

Yield, 85.2%.
IR (cm⁻¹) 3300, 2100, 1760, 1610, 1510.
¹H-NMR (δ, ppm) 2.40 (CH≡C—), 4.87 (≡C—CH₂—), 7.10, 7.95 (Ph)

EXAMPLE 23

4-Propargyloxycarbonyloxybiphenyl

Yield, 90.2%.
IR (cm⁻¹) 3300, 2100, 1760, 1610, 1510.
1H-NMR (δ, ppm) 2.2.40 (CH≡C—), 4.87 (≡C—CH₂—), 7.10, 7.95 (Ph).

EXAMPLE 24

1-Propargyloxycarbonyloxynaphthalene

Yield, 83.2%.
IR (cm⁻¹) 3300, 2100, 1760, 1610, 1510.
¹H-NMR (δ, ppm) 2.42 (CH≡C—), 4.88 (≡C—CH₂—), 7.10, 7.95 (Ph).

EXAMPLE 25

3,3'-Dimethyl-4,4'-bis(propargyloxycarbonyloxy)-biphenyl

Yield, 93.6%.
IR (cm⁻¹) 3300, 2110, 1750, 1600, 1500.
¹H-NMR (δ, ppm) 2.55 (CH≡C—), 4.86 (≡C—CH₂—), 7.30, 7.90 (Ph).

EXAMPLE 27

Analogous to Example 19, one mole of biphenyl-4,4'-bischloroformate was reacted with two moles of propargyl alcohol. The product was identified to be the same as the product of Example 19 in the IR spectrometry and ¹H-NMR. Yield, 63.6% of theory.

What is claimed is:

1. A compound of the formula:

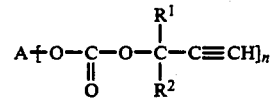

wherein
A is a system having two benzene rings linked together with
—S—, —O— or —SO₂—, said benzene rings optionally having up to four substituents thereon selected from the group consisting of a $C_1$-$C_{12}$ alkyl, a $C_1$-$C_{12}$ alkoxy, halo, nitro and cyano;
$R^1$ and $R^2$ are independently a hydrogen atom or $C_1$-$C_{12}$ alkyl; and
n is an integer of 1, 2 or 3.

2. The compound as claimed in claim 1, wherein $R^1$ and $R^2$ each is a hydrogen atom.

3. The compound as claimed in claim 2, wherein said system is diphenylsulfone.

4. The compound as claimed in claim 2, wherein said system is benzophenone.

5. The compound as claimed in claim 1 which is 4,4'bis(4-propargyloxycarbonyloxyphenyl) sulfone.

6. The compound as claimed in claim 1 which is 4,4'-bis(propargyloxycarbonyloxy)benzophenone.

7. The compound as claimed in claim 1, which is bis(3,3-dibromo-4-propargyloxycarbonyloxyphenyl)-sulfone.

8. The compound as claimed in claim 1, which is bis[4-(1,1-dimethyl-2-propinyl)oxycarbonyloxyphenyl]-sulfone.

* * * * *